United States Patent [19]

Prasad

[11] Patent Number: 5,423,680

[45] Date of Patent: Jun. 13, 1995

[54] PALLADIUM, GALLIUM AND COPPER-FREE ALLOY HAVING HIGH THERMAL EXPANSION COEFFICIENT

[75] Inventor: Arun Prasad, Cheshire, Conn.

[73] Assignee: Jeneric/Pentron, Incorporated, Wallingford, Conn.

[21] Appl. No.: 149,739

[22] Filed: Nov. 10, 1993

[51] Int. Cl.⁶ .......................... C22C 5/02; C22C 5/04; C22C 5/06; C22C 27/02
[52] U.S. Cl. ................................. 433/207; 433/200.1; 148/422; 148/430; 148/442; 420/425; 420/426; 420/427; 420/505; 420/507; 420/510; 420/511; 420/512; 420/580
[58] Field of Search ............... 420/508, 509, 510, 511, 420/580, 425, 426, 427, 505, 512, 507; 148/430, 422; 433/200.1, 207

[56] References Cited

U.S. PATENT DOCUMENTS

| | | | |
|---|---|---|---|
| 3,981,723 | 9/1976 | Tuccillo | 420/508 |
| 4,062,676 | 12/1977 | Knosp | 420/510 X |
| 4,201,577 | 5/1980 | Ingersoll et al. | 420/508 |
| 4,297,266 | 10/1981 | Ibsen et al. | 260/42.14 |
| 4,604,366 | 8/1986 | Kacicz et al. | 501/6 |
| 5,221,207 | 6/1993 | Schoeck et al. | 433/207 |
| 5,276,068 | 1/1994 | Waknine | 433/222.1 X |

FOREIGN PATENT DOCUMENTS 1132728  5/1989  Japan.

*Primary Examiner*—David A. Simmons
*Assistant Examiner*—Sean Vincent
*Attorney, Agent, or Firm*—Watson, Cole, Grindle & Watson

[57] ABSTRACT

A dental alloy is provided which is free of palladium, gallium and copper and which is compatible with a wide variety of composites and porcelain compositions. The alloy has a melting range of between about 870° C. and 1230° C. and a coefficient of thermal expansion of between $15.5 \times 10^{-6}$ and $17.5 \times 10^{-6}$ in/in/° C. when heated from room temperature to 500° C. The alloy contains between about 40 and 80 percent by weight gold, between 5 and 50 percent by weight of thermal expansion adjuster, between two and 15 percent by weight strengthener and oxide former, up to about 1.5 percent by weight grain refiner, and up to about 0.25 percent by weight deoxidizer.

15 Claims, No Drawings

PALLADIUM, GALLIUM AND COPPER-FREE ALLOY HAVING HIGH THERMAL EXPANSION COEFFICIENT

FIELD OF THE INVENTION

The present invention relates to dental alloys which have high coefficients of thermal expansion. The alloys can be coated with composite or porcelain compositions which also have high thermal expansion coefficients and fired to form finished restorations.

BACKGROUND OF THE INVENTION

Dental copings or posts coated with a dental porcelain have been used in restorations of single or multiple teeth. The jacket or covering of dental porcelain on the metal coping or post provides a restoration which closely resembles a natural tooth. Dental crown and bridge restorations are often made with a metal base comprising a malleable metal alloy which is gentle on opposing dentition. Both types of restorations are well known and have been used for many years.

The general technique for the construction of a porcelain coated dental restoration involves first taking an impression of a denture area that has been prepared to receive the restoration. A die is prepared from the impression, and a metal base ("coping" or "post") is cast to fit the die. The metal base has an internal shape to match the prepared denture. A porcelain powder is then mixed with water to form a slurry which is then applied to the metal base, or a portion of a metal base, by standard procedures. The slurry is shaped in the form of the finished tooth, crown, multiple unit bridge, inlay or onlay. Alternatively, a resin-containing composite may be used to form the outer coating of the restoration. The porcelain is then dried, and fired in a furnace at a desired firing temperature. The restoration may be fired several times before the final form is obtained, and the porcelain may be applied in several layers.

To form a strong bond between a dental porcelain and a dental alloy, it has been determined that the temperature range in which the glass-forming components of a porcelain composition melt and mature should be slightly below the melting point of the dental alloy. Herein, the temperature or temperature range in which the glass-forming particles in the porcelain mixture melt to form a glass melt is referred to as the fusion temperature or the fusion temperature range. To form a strong bond, it is also important that the thermal expansion coefficient of the porcelain be close to, but slightly less than, that of the dental alloy.

There is a significant temperature change when heating a restoration from room temperature to the firing temperature, as occurs when a restoration is alternately fired and cooled. Therefore, significant stress can be induced in the restoration if the thermal expansion of the porcelain coating does not closely match that of the dental alloy base.

Crown and bridge alloys have different properties when compared to traditional ceramic alloys used with a fused porcelain veneer. Crown and bridge alloys have a lower casting temperature and a higher coefficient of thermal expansion than traditional ceramic alloys. Traditional porcelains would not bond strongly to crown and bridge alloys due to the large difference in thermal expansion coefficients of the alloys and the porcelains. It is desirable to develop a dental restoration system which provides the convenience of a low casting temperature and high expanding alloy with a dental porcelain having a correspondingly high thermal expansion coefficient.

Table I below shows the melting or fusion temperature range of traditional ceramic alloys, traditional dental porcelains and crown and bridge alloys.

TABLE I

| | MELTING/FUSION TEMP. RANGE (°C.) | COEF. of THERM. EXP. (in/in/°C.) (RT-500°C.) |
|---|---|---|
| CERAMIC ALLOYS | 1050–1300 | 13.6–15 × 10$^{-6}$ |
| TRADITIONAL PORCELAIN | 925–1000 | 12.7–14 × 10$^{-6}$ |
| CROWN AND BRIDGE ALLOYS | 815–1000 | 15.5–18.3 × 10$^{-6}$ |

Recently, many dental porcelains have been developed which exhibit high coefficients of thermal expansion. To be successfully used in dental restorations, such porcelains must be used with correspondingly high expanding dental alloy bases or copings. It is desirable to provide a family of dental alloys having coefficients of thermal expansion which exceed $15 \times 10^{-6}$ in/in/° C. when heating from room temperature to 500° C. and which can be used with a wide variety of high thermal expansion dental porcelains.

Dental alloy bases that are most often employed today in such restorations include gold, high and low gold alloys including gold-palladium alloys, silver-palladium alloys, high palladium alloys, nickel-chrome-molybdenum type alloys, gold-silver-palladium alloys and palladium-copper alloys. Gold and its alloys are preferred metals for a metal base due to their biocompatibility with the human body. Precious metal alloys exhibit thermal expansion coefficients of about $13.6 \times 10^{-6}$ to $18.3 \times 10^{-6}$ in/in/° C. and thus ceramics which are used with gold metal and alloys should have similar thermal expansion coefficients. Many additives have been used to alter and improve the properties of gold and gold alloys. Among such additives are palladium, gallium and copper.

Recently, there has become a heightened concern among dentists and patients as to whether alloys comprising palladium, gallium or copper are completely safe. It is feared that these elements may not be as biocompatible with the human body as once thought. While there is no scientific proof of any unsafe qualities of dental alloys containing these elements, it is nonetheless desired by some dentists and patients to use dental alloys which do not contain these elements.

SUMMARY OF THE INVENTION

It is an object of the present invention to provide a dental alloy specifically formulated to be highly biocompatible with the human body. More particularly, it is an object of the present invention to provide a dental alloy which is free of palladium, gallium and copper.

It is also an object of the present invention to provide a dental alloy specifically formulated to be compatible with high thermal expansion dental porcelains and composites. More particularly, it is an object of the present invention to provide a dental alloy having a coefficient of thermal expansion when heated from room temperature to 500° C. of higher than about $15 \times 10^{-6}$ in/in/° C.

It is also an object of the present invention to provide a dental alloy which has a melting range of between about 870° C. and 1230° C.

According to one embodiment of the present invention, a dental alloy is provided which has both a melting range between 870° C. and 1230° C. and a coefficient of thermal expansion which is between $15.5 \times 10^{-6}$ and $17.5 \times 10^{-6}$ in/in/° C. when heated from room temperature to 500° C.

The present invention also encompasses alloys which would traditionally be considered crown and bridge alloys, but which can be coated with porcelain compositions to form more complicated, natural-looking dental restorations. Crown and bridge alloys, by definition, have been used to make dental restorations which are not coated with porcelains or composites. However, according to an embodiment of the present invention, alloys of this type are provided which are capable of being coated with a porcelain or composite. Herein, the alloys of the present invention will be referred to as dental alloys, and include alloys which would traditionally be thought of as useful for crown and bridge alloys.

According to one embodiment, the alloys of the present invention can be cast to include full cast crowns/bridges and a substrate which can be entirely or partially coated with a dental porcelain to form a desired restoration. It may be desired to coat only a portion of a multiple unit bridge.

The above and other objects may be achieved according to the present invention by providing a dental alloy which comprises between about 40 and 80 percent by weight gold, between 5 and 50 percent by weight of a thermal expansion adjuster, between two and ten percent by weight of strengtheners and oxide formers, up to about 1.5 percent by weight grain refiner, and up to about 0.25 percent by weight deoxidizer.

The thermal expansion adjuster preferably is at least one member selected form the group consisting of platinum, niobium, tantalum and silver. The strengthener and oxide former preferably comprises at least one member selected from the group consisting of indium, tin, manganese, zinc, iron, chromium, titanium and germanium. The grain refiner preferably comprises at least one member selected from the group consisting of iridium, ruthenium, rhenium, rhodium and cobalt. The deoxidizer comprises at least one member selected from the group consisting of calcium, boron, silicon, aluminum, lithium and phosphorus.

The invention may be more fully understood with reference to the detailed description which follows. The invention is not limited to the exemplary embodiments but should be recognized as contemplating all modifications within the skill of an ordinary artisan.

DETAILED DESCRIPTION OF THE INVENTION

The dental porcelains according to the present invention are formulated to have a coefficient of thermal expansion which is between $15.5 \times 10^{-6}$ and $17.5 \times 10^{-6}$ in/in/° C. when heated from room temperature to 500° C., and a melting temperature of between 870° C. and 1230° C. The alloys of the present invention are particularly well suited for being coated with a wide variety of composites and porcelain compositions. Preferably, the alloy exhibits a yellow color.

The dental alloys according to the present invention comprise between about 40 and 80 percent by weight gold, between 5 and 50 percent by weight of a thermal expansion adjuster, between two and ten percent by weight of strengtheners and oxide formers, up to about 0.1 percent by weight grain refiner, and up to about 0.1 percent by weight deoxidizer.

The thermal expansion adjuster preferably comprises at least one member selected form the group consisting of platinum, niobium, tantalum and silver. The strengthener and oxide former preferably comprises at least one member selected from the group consisting of indium, tin, manganese, zinc, chromium, titanium, iron and germanium. The grain refiner preferably comprises at least one member selected from the group consisting of iridium, ruthenium, rhenium, rhodium and cobalt. The deoxidizer comprises at least one member selected from the group consisting of calcium, boron, silicon, titanium, aluminum, lithium and phosphorus.

The dental alloys according to the present invention comprise between 40 and 80 percent by weight gold. According to the present invention, alloys comprising between about 50 and 77 percent by weight gold are preferred while those having between about 50 and 75 percent by weight are even more preferred. The gold provides a desirable yellow coloration to the restoration base. Also, gold is preferred in dental alloys because it is highly biocompatible with the human body.

The thermal expansion adjuster is preferably at least one member selected form the group consisting of platinum, niobium, tantalum and silver. In one embodiment, the alloys more preferably comprise both platinum and silver. In particular, some preferred alloys of the present invention comprise between five and ten percent by weight platinum and between 10 and 15 percent by weight silver.

Generally, the property of thermal expansion is inversely related to the melting point or range of an alloy. Platinum raises the melting point or range when added to gold alloys. Likewise, platinum may be added to lower the coefficient of thermal expansion of the alloy. Silver may be added to lower the melting point or range of a gold alloy and likewise raise thermal expansion properties of the alloy.

The addition of platinum and silver dilutes the yellow color of the gold without substantial loss of resistance to corrosion and tarnish.

A mixture of both platinum and silver is preferred because combinations of platinum and silver may be used to provide a gold alloy having a specific melting range, or a specific coefficient of thermal expansion. The choice of specific thermal expansion adjusters and the amount of each to use is largely dependent on the atmosphere under which the alloy is to be melted prior to the casting. For example, if the alloy is to be melted by a gas flame (e.g. oxygen), tantalum should be used only in small quantity.

The selection of an element or combination of elements from this group may also be dependent on the thermal expansion coefficient of the overlay material. The thermal expansion of the alloy is preferably adjusted to be slightly greater than the thermal expansion of the overlay material. Matching the thermal expansions in this manner enables the formation of compressive stress at the interface between the alloy and the overlay material. Achieving this condition strengthens the overlay material which is generally weaker than the alloy substrate.

Alloys consisting of gold and at least one of platinum, and silver are relatively weak and can be used only in low stress-bearing areas. In order to extend the application of such alloys to a use in areas of high masticatory stress, they must further be strengthened. A strengthener and oxide former may be used for this purpose.

The strengtheners and oxide formers used in the alloys of the present invention preferably comprise at least one member selected from the group consisting of indium, tin, manganese, zinc, chromium, titanium, iron and germanium. These elements not only strengthen the alloy but also allow the formation of adherent oxides, which are responsible for the chemical bonding of porcelains and composite coatings to the alloy.

These strengthening elements also contribute to the control of the melting point or range of the alloy as well as thermal expansion properties. The amount of strengthening elements for use in alloys to which a dental porcelain will be fused is dictated by the fusion range of the porcelain. If the porcelain is a lower fusing porcelain, higher amounts of these elements can be used without causing the alloy to become too brittle.

Of the identified strengtheners and oxide formers, tin, zinc and indium are preferred with tin and zinc being more preferred.

Grain refiners are added to the alloy to control grain size by providing nucleating sites as the alloy melt solidifies. The smaller the grain size, the better the formability of the alloy and the greater the number of grains over the thickness of alloy. Smaller grain sizes also improve the ability of the alloy to be polished once cast, and improves resistance to both corrosion and tarnishing. Smaller grain sizes also make the alloy less vulnerable to heat tears or cracks during casting of thin wall copings. Smaller grain size in an alloy additionally enables the edges and margins of the casting to be non-ragged and easily burnished. A margin is defined herein as the area where the dental coping comes in contact with the gum tissue.

According to the present invention, the grain refiner preferably comprises at least one member selected from the group consisting of iridium, ruthenium, rhenium, rhodium and cobalt. Preferably, grain refiner is added in an amount sufficient to control grain size and to improve the formability, polishibility and corrosion and tarnish resistance when compared to the same alloy without a grain refiner. Up to about 0.1 percent by weight is all that is required although greater amounts may be used. Of the identified grain refiners, iridium is the most preferred.

Deoxidizers are added to alloys to prevent the loss of important ingredients of the alloy during heating and melting operations. Deoxidizers prevent such loss by sacrificing themselves. They also act as scavengers to rid the melt of gaseous inclusions. Although the present invention is not limited to alloys which contain a deoxidizer, without the addition of an oxidizer, bubbling may develop during the firing cycle.

According to the present invention, the deoxidizer comprises at least one member selected from the group consisting of calcium, boron, silicon, aluminum, lithium and phosphorus. Of these, calcium and boron are preferred. Preferably, the deoxidizer is present in an amount sufficient to substantially prevent the oxidation of other metals in the alloy during alloy melting, rid the alloy of gaseous inclusions once it has been melted, and substantially prevent bubbling of the alloy during porcelain firing cycles. Amounts up to 0.25 percent by weight deoxidizer may be used, with amounts of up to 0.1 percent being preferred for some embodiments.

Calcium is a very potent deoxidizer and is likewise very reactive. Unfortunately, elemental calcium is difficult to handle because it so readily reacts with humidity in the air and oxidizes. Boron is not as potent a deoxidizer but may be used in combination with calcium to minimize oxidation of the calcium. For example, $CaB_6$ is a preferred deoxidizer in the alloys of the present invention.

Table II below shows a number of examples of alloys made in accordance with the present invention.

TABLE II

| Component | EXAMPLE NO. | | | |
|---|---|---|---|---|
| | I | II | III | IV |
| Au | 75.00 | 74.00 | 60.00 | 50.00 |
| Pt | 8.50 | 8.50 | 9.00 | 8.00 |
| Ag | 12.40 | 13.40 | 25.00 | 38.00 |
| In | 2.00 | 2.00 | — | 2.00 |
| Mn | 1.00 | 2.00 | — | — |
| Sn | — | — | 4.00 | — |
| Zn | 1.00 | — | 1.90 | 1.90 |
| Ir | 0.05 | 0.05 | 0.05 | 0.05 |
| $CaB_6$ | 0.05 | 0.05 | 0.05 | 0.05 |

Examples I, II, III and IV exhibit coefficient of thermal expansion values of 15.5 and $17.5 \times 10^{-6}$ in/in/° C., respectively. Their melting ranges lie between 870° C. and 1230° C. The yield strength values vary between 40,000 psi and 100,000 psi and the elongation values fall between two percent and 25 percent.

What follows is a description of some exemplary porcelains which may be used to coat the alloys of the present invention. The present invention is not limited to restorations comprising the described porcelains.

A wide variety of porcelain mixtures form desirable porcelain coatings when fused to dental alloys. Different mixtures are preferred for the different layers of the restoration. The restoration may preferably comprise a bond layer, an opaque porcelain layer, a body layer and an incisal layer.

Differences in the components used for each layer and differences in the amounts of the components enable the different layers to exhibit different optical and thermal properties.

A preferred porcelain will have a fusion range of 725° C. to 850° C. and a coefficient of thermal expansion between $15.0 \times 10^{-6}$ to $17.0 \times 10^{-6}$ in/in/° C. when heated from 25 to 500° C. The dental porcelain may comprise oxides of Si, Al, K, Na, Li, Ca, Mg, Zr, Sn, Ti, Y, Ce and Eu. Some preferred porcelain compositions contain at least 33 percent by weight leucite. Preferred porcelains may also contain various pigments for coloration and hydroxyl and fluoride groups in their glass network.

A wide variety of composites can also be used and include those made of glass fillers and resins such as Bis-GMA, TEGDMA, UDMA and PCDMA. The composites may be cured by means such as photo-initiation, chemical curing, combinations of photo-initiation and chemical curing, and heat curing. The curing may also be cured under water, under vacuum and under pressure of inert gases. One such composite is available as Conquest ® from Jeneric/Pentron Inc., Wallingford, Conn.

Although the present invention has been described in connection with preferred embodiments, it will be appreciated by those of skill in the art that additions, modifications, substitutions and deletions not specifically described may be made without departing from the spirit and scope of the invention defined in the appended claims.

We claim:

1. A dental alloy which can be coated with a composite or a porcelain composition to form a dental restoration, said alloy comprising:
   (A) between 40 and 80 percent by weight gold;
   (B) between five and 50 percent by weight of thermal expansion adjuster selected from the group consisting of platinum, silver, niobium and tantalum;
   (C) between about two and about ten percent by weight strengthener and oxide former comprising at least one member selected from the group consisting of indium, tin, manganese, zinc, chromium, titanium, iron and germanium;
   (D) up to about 1.5 percent by weight grain refiner comprising at least one member selected from the group consisting of iridium, ruthenium, rhenium, rhodium and cobalt; and
   (E) up to about 0.25 percent by weight deoxidizer comprising at least one member selected from the group consisting of calcium, boron, silicon aluminum, lithium and phosphorus said alloy being free of palladium, gallium and copper, having a melting range of between 870° C. and 1230° C., and having a coefficient of thermal expansion between $15.5 \times 10^{-6}$ and $17.5 \times 10^{-6}$ in/in/° C. when heated from room temperature to 500° C.

2. A dental alloy as defined in claim 1, wherein component (D) comprises iridium present in an amount of up to about one percent by weight.

3. A dental alloy as defined in claim 1, wherein component (D) comprises iridium present in an amount of up to about 0.1 percent by weight.

4. A dental alloy as defined in claim 1, wherein component (D) comprises ruthenium present in an amount of up to about one percent by weight.

5. A dental alloy as defined in claim 1, wherein component (E) is present in an amount of up to about 0.1 percent by weight.

6. A dental alloy as defined in claim 1, wherein component (E) comprises at least one member selected from the group consisting of calcium and boron.

7. A dental alloy as defined in claim 1, wherein said alloy exhibits a yellow color.

8. A dental restoration comprising a dental alloy coated with a dental porcelain composition, wherein said dental alloy comprises:
   (A) between 40 and 80 percent by weight gold;
   (B) between five and 50 percent by weight of thermal expansion adjuster selected from the group consisting of platinum, silver, niobium and tantalum;
   (C) between about two and about ten percent by weight strengthener and oxide former comprising at least one member selected from the group consisting of indium, tin, manganese, zinc, chromium, titanium, iron and germanium;
   (D) up to about 1.5 percent by weight grain refiner comprising at least one member selected from the group consisting of iridium, ruthenium, rhenium, rhodium and cobalt; and
   (E) up to about one percent by weight deoxidizer comprising at least one member selected from the group consisting of calcium, boron, silicon, aluminum, lithium and phosphorus, said alloy being free of palladium, gallium and copper, having a melting range of between 870° C. and 1230° C., and having a coefficient of thermal expansion between $15.5 \times 10^{-6}$ and $17.5 \times 10^{-6}$ in/in/° C. when heated from room temperature to 500 ° C.

9. A dental restoration alloy as defined in claim 8, wherein said alloy exhibits a yellow color.

10. A dental restoration alloy as defined in claim 8, wherein said porcelain comprises at least 33 percent by weight $K_2O.Al_2O_3 \cdot 1.4SiO_2$.

11. A dental restoration comprising a dental alloy coated with a dental composite, wherein said dental alloy comprises:
   (A) between 40 and 80 percent by weight gold;
   (B) between five and 50 percent by weight of thermal expansion adjuster selected from the group consisting of platinum, silver, niobium and tantalum;
   (C) between about two and about ten percent by weight strengthener and oxide former comprising at least one member selected from the group consisting of indium, tin, manganese, zinc, chromium, titanium, iron and germanium;
   (D) up to about 1.5 percent by weight grain refiner comprising at least one member selected from the group consisting of iridium, ruthenium, rhenium, rhodium and cobalt; and
   (E) up to about 0.25 percent by weight deoxidizer comprising at least one member selected from the group consisting of calcium, boron, silicon, aluminum, lithium and phosphorus, said alloy being free of palladium, gallium and copper, having a melting range of between 870° C. and 1230° C., and having a coefficient of thermal expansion between $15.5 \times 10^{-6}$ and $17.5 \times 10^{-6}$ in/in/° C. when heated from room temperature to 500° C.

12. A dental restoration as defined in claim 11, wherein said alloy exhibits a yellow color.

13. A dental restoration as defined in claim 11, wherein said dental composite comprises a resin selected from the group consisting of Bis-GMA, TEGDMA, UDMA and PCDMA.

14. A dental restoration as defined in claim 13, wherein said dental composite comprises polycarbonate dimethacrylate.

15. A dental alloy which can be coated with a composite or a porcelain composition to form a dental restoration, said alloy comprising:
   (A) between 40 and 80 percent by weight gold;
   (B) between five and 50 percent by weight of thermal expansion adjuster selected from the group consisting of platinum, silver, niobium and tantalum;
   (C) between about two and about ten percent by weight strengthener and oxide former comprising at least one member selected from the group consisting of indium, tin, manganese, zinc, chromium, titanium, iron and germanium;
   (D) up to about 1.5 percent by weight grain refiner comprising at least one member selected from the group consisting of iridium, ruthenium, rhenium, rhodium and cobalt; and
   (E) deoxidizer present in an amount of up to about 0.25 percent by weight, said deoxidizer comprising at least one member selected from the group consisting of calcium and boron, and wherein said alloy is free of palladium, gallium and copper and has a melting range of between 870° C. and 123° C., and has coefficient of thermal expansion between $15.5 \times 10^{-6}$ and $17.5 \times 10^{-6}$ in/in/° C. when heated from room temperature to 500° C.

* * * * *